United States Patent [19] [11] Patent Number: 5,035,862
Dietze et al. [45] Date of Patent: Jul. 30, 1991

[54] ANALYTICAL SYSTEM FOR THE DETERMINATION OF A COMPONENT OF A FLUID

[75] Inventors: Werner Dietze, Tutzing; Rainer Füllemann, Weinheim; Thomas Lutz, Mannheim, all of Fed. Rep. of Germany

[73] Assignee: Boehringer Mannheim GmbH, Mannheim, Fed. Rep. of Germany

[21] Appl. No.: 282,107

[22] Filed: Dec. 9, 1988

[30] Foreign Application Priority Data

Dec. 17, 1987 [DE] Fed. Rep. of Germany ....... 3742786

[51] Int. Cl.⁵ ............................................. G01N 25/00
[52] U.S. Cl. .................................... 422/68.1; 422/58; 422/104; 436/157; 436/169
[58] Field of Search ............... 422/68.1, 66, 104; 436/155, 157, 169; 435/805; 219/10.57, 10.75

[56] References Cited

U.S. PATENT DOCUMENTS 3,932,133 1/1976 Ishikawa ............................ 422/55
4,160,008 7/1979 Fenocketti et al. ............... 435/805
4,163,139 7/1979 Malarkey et al. ................. 219/10.75
4,605,629 8/1986 Lange et al. ....................... 436/169
4,647,431 3/1987 Sekine et al. ...................... 422/99

FOREIGN PATENT DOCUMENTS 905047 6/1944 France .

Primary Examiner—Robert J. Warden
Assistant Examiner—Laura E. Collins
Attorney, Agent, or Firm—Felfe & Lynch

[57] ABSTRACT

An analytical system for the determination of a component of a fluid, especially blood or urine, is disclosed. It comprises test carriers, which have at least one test field, and an evaluating instrument for the measurement of a characteristic change in the test field.

In order to achieve rapid and selective heating of individual test fields, especially in test carriers that are multiple-test strips, the corresponding test field has a metallic conducting layer, which runs parallel to the test field and is in thermal contact with it. The evaluating instrument has an induction heater. The guiding mechanism of the test carrier in the evaluating instrument is designed so that the metallic conducting layer, at least before the measurement, is in the working area of the alternating magnetic field emanating from the induction heater.

8 Claims, 1 Drawing Sheet

ANALYTICAL SYSTEM FOR THE DETERMINATION OF A COMPONENT OF A FLUID

BACKGROUND OF THE INVENTION

The invention is directed to an analytical system for the determination of a component of a fluid with a test carrier, which has at least one test field, and an evaluating instrument for the measurement of a change in the test field that is characteristic of the concentration of the component to be determined. A temperature conditioner is provided to heat the test field to an elevated temperature before the evaluation.

For the qualitative or quantitative analytical determination of fluids, especially body fluids such as blood and urine, so-called carrier-bound tests are being used more and more. For these tests, reagents are embedded in the dry state in appropriate test fields of a test carrier. When the test field is brought into contact with the sample, the reaction of sample and reagent leads to a measurable change in the test field.

Evaluating instruments are used to measure the change in the test field caused by the reaction. This change generally consists of a color change, the reflection of which is measured photometrically by the instrument. However test carriers working on the basis of other physical quantities, such as the fluorescence, are also known.

The test carriers frequently are constructed as test strips, in which one or several test fields are applied to a longitudinal carrier of synthetic resin material. However, test carriers in the form of square or rectangular platelets are also known. The evaluating instruments usually are matched to test carriers of a particular type from a particular manufacturer. The test carrier and evaluating instrument form an analytical system.

It is frequently desirable to heat test fields to an elevated temperature during the reaction. This is generally accomplished by pressing the test field side or even the reverse side of the test carrier against a heated metal surface. Alternatively, incubation chambers having an elevated temperature are used in which the test carriers remain in the time period between the application of the sample and the evaluation. Frequently, an acceleration of the reaction and an increase in detection sensitivity can be achieved by heating.

Previously used methods, however, are not satisfactory in every respect. Above all, the heating is very slow. Moreover, it is not possible to heat narrow spatial areas selectively, as is particularly desirable for multiple-test strips for urine analysis. The various test fields of such a multiple test strip frequently work optimally at different temperatures. Considerable difficulties have been encountered in modifying the chemical composition of test fields so that all could be evaluated at the same temperature. It would be substantially simpler if it were possible to heat the individual test fields selectively and rapidly, without affecting the adjacent test fields.

SUMMARY OF THE INVENTION

Rapid and selective temperature conditioning of the test fields of test carriers is accomplished with an analytical system in which the test carrier has at least one metallic conducting layer that is assigned to the test field, runs parallel to the test field and is in thermal contact with it. The evaluating instrument has an induction heater that produces an alternating magnetic field, and the guiding system of the test carrier in the evaluating instrument is designed so that the metallic conducting layer is in the effective region of the alternating magnetic field at least before the measurement.

The metallic conducting layer may, for example, comprise a metallized plastic. Particularly simple and well suited is a metal foil, especially of aluminum or copper, with a thickness of less than 0.5 mm and preferably of about 0.2 mm.

In certain application cases, it may be appropriate to use a metallic conducting layer of a ferro-magnetic material. The heat due to energy losses during magnetic reversal in such a material when in the alternating magnetic field, leads to particularly rapid heating of the layer.

As mentioned before, the invention is especially suitable for use with multiple-test strips, because it makes possible a selective heating of individual test fields. In this case, a metallic conducting layer is provided only for these heated test fields. If different test fields are to be heated differently, this can be accomplished appropriately by assigning metallic conductive layers of different thickness and/or of different materials to the test fields.

The invention proves to be exceptionally advantageous in practice:

Although anyone skilled in the art is familiar with the advantages of heating during the course of the reaction, heating of test fields frequently was avoided in the past, because it led to an inadmissible evaporation of sample. Because of the unusually rapid heating that is provided in accordance with the invention, the evaporation is so slight that it does not interfere with the measurement.

Due to the selective heating, the energy consumption is very low. The invention, therefore, provides temperature conditioning that is particularly suitable for battery equipment.

Within the limits of the tolerances of the test carrier guiding system present in conventional evaluating instruments, the temperature conditioning is largely independent of the distance between the induction heaters.

The temperature conditioning is practically independent of air currents in the vicinity of the test strip.

Through inductive coupling with the inductive heater, the metallic conducting layer additionally permits to localize the respective test field in the equipment.

DESCRIPTION OF A PREFERRED EMBODIMENT

Figure 1:
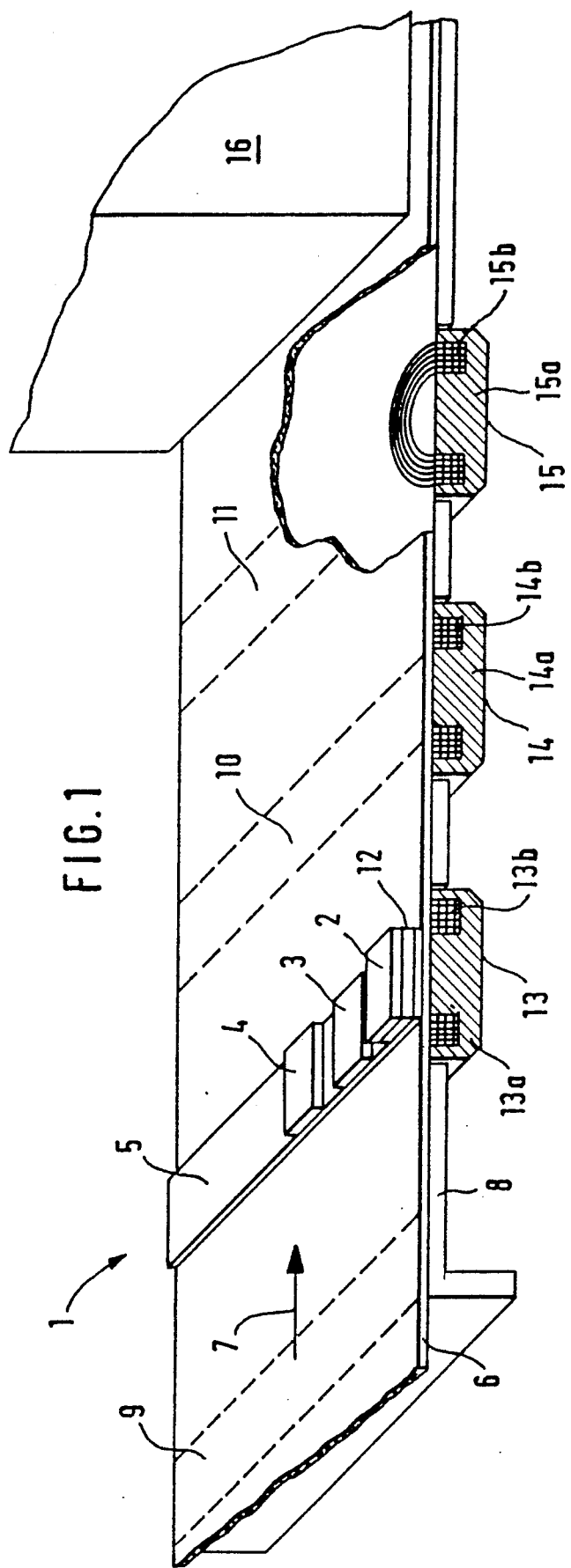
FIG. 1 shows an analytical system in accordance with the present invention in a partially cross-sectional perspective representation.

In FIG. 1, a portion of the test carrier evaluating instrument is shown, which serves as inlet, for temperature conditioning and for the photometric measurement. The test carrier shown is a multiple-test strip 1 with several adjacently arranged test fields 2, 3, 4, which are mounted on a base layer 5. Such multiple-test strips are known. They are immersed in a urine sample. After a predetermined incubation time, the color change of the test fields is evaluated visually or by an instrument. Each test field serves for the detection of a particular component. The test fields therefore differ in their chemical composition and in their physical, frequently multilayer construction.

The test strips, with the help of a sheet of absorptive paper 6, are conveyed in the direction of the arrow 7 from left to right over a level transport table 8. The test strips adhere adequately to the sheet of paper 6, since they are moist after the immersion in the urine. For the sake of clarity, only one test strip is shown in FIG. 1. Normally, however, several test strips are placed on the paper sheet 6. They are spaced equally far apart and are evaluated consecutively. The corresponding positions 9, 10, 11 on the paper sheet 6 are indicated by broken lines in the Figure.

The paper sheet 6 is transported in a stepwise manner. The length of the steps correspond to the distance between the test strips 1. A uniform distance between the test strips can easily be achieved by placing them on the stationary paper sheet 6 at locations indicated by a suitable guide or marking.

Below the test field 2, there is a metal foil 12, which may be glued on a base layer 5, for example. The test field 2 is then in turn glued onto the metal foil 12.

Several induction heaters 13, 14 and 15 are embedded in the transport table 8. In each case, they comprise a ferrite core 13a, 14a, 15a and a coil 13b, 14b, 15b. In the area of the induction heater 15, the paper sheet is shown cut open, so that the circular construction of the core and the coil can be seen.

To heat it to an elevated temperature, the test field must be brought to the working area of an induction heater. In FIG. 1, a magnetic field emanates from the induction heater 13, when an alternating current flows through coil 13b of heater 13. The corresponding test field of a test strip, lying on positions 10 and 11, is in the working area of the alternating magnetic field emanating from the induction heaters 14, 15. Generally the metallic conducting layer 12 has to be in the working area of the magnetic field in the sense that it has to be positioned in the range of that field such that an effective heating is achieved due to the electric current inductively generated by the field. Preferably the distance between the coil 13b and the metal foil 12 should be as short as possible. In practice, a distance of 3 to 5 mm has proven especially satisfactory.

Coil 13b is put into operation by applying an alternating electric voltage. A frequency of 50 kHz has proven satisfactory in practice. Voltage sources providing adequate power in the suitable frequency range are commercially available and, therefore, do not have to be described in greater detail.

Eddy currents are induced in the metal foil 12 by the alternating magnetic field. They produce thermal energy that heats the metal foil 12 and, thus, the test field 2. The entire surface of the test field 2 touches the metal foil, thus producing good thermal contact.

When a test carrier 1, as mentioned, is transported stepwise over the transport table 8, the position of the test strip shown in the Figure and the positions 10 and 11 forming equidistant stopping points at which in each case an inductive heater is provided, inductive heating of the test field by the induction heaters 13, 14, 15 can take place during pauses between the transporting steps.

Surprisingly, the application of intermittent heat leads to a largely constant heating of the test field. The induction heater 13 that first heats the test field 2 is operated with an appreciably higher power to ensure rapid heating. The other induction heaters 14, 15 then serve merely to keep the temperature constant. The heat output of the first induction heater 13 is at least twice that of the subsequent heaters.

After temperature conditioning, the test strips reach a photometer 16, in which the color change on the test fields is measured. The design of the photometer unit 16 is not important for the invention. It is however, important that the photometric measurement takes place in a position that corresponds to a stop in the stepwise transport of the test strip.

As a test field that is provided with a metal foil enters the working area of an induction heater, the electromagnetic properties of the working area are changed by inductive coupling between the metal foil and the coil. By detecting a parameter such as the change in the amperage in the primary circuit of the coil by using one of the suitable circuits known in the art, it is possible to check whether the test carrier is positioned correctly over the respective induction heater.

Figure 2:
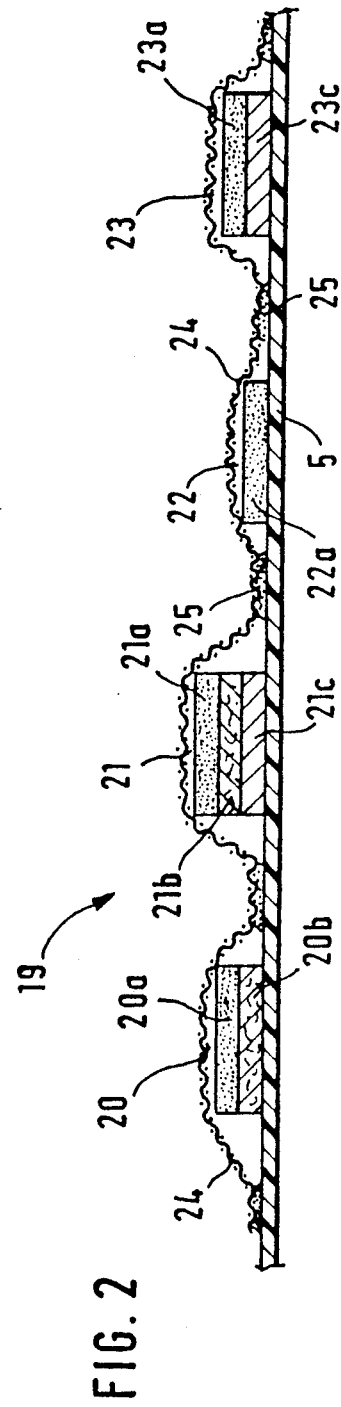
FIG. 2 shows a longitudinal cross section through a test carrier for an analytical system in accordance with the present invention.

FIG. 2 is a detailed representation of a multiple-test strip 19, like those that are particularly suitable for an inventive analytical system. On the base layer 5, several test fields 20, 21, 22 and 23 are disposed, some of which have a multilayer construction. The test fields are secured with the help of a net 24, which is stretched over them and which is connected in the fastening areas 25 with melt adhesives to the base layer 5 which is usually a plastic film. The individual layers of the test carrier preferably are prepared separately and secured only by the net 24.

The test field 20 comprises a reagent layer 20a and backing paper 20b. The test field 21 comprises a reagent layer 21a and a backing paper 21b. Underneath, there is a metal foil 21c. The test field 22 comprises only the reagent layer 22a. A metal foil 23c is clamped below the reagent layer 23a of the test field 23.

It is evident from FIG. 2 that the individual test fields may be constructed very differently. In the present case two test fields, namely test fields 21 and 23, are provided with a metal foil so that they can be heated inductively. In the case of test field 23, thermal contact between the metal foil and the reagent field is readily ensured, because the complete surfaces of the two layers are in contact.

Test field 21 illustrates that the invention is not limited to such simple cases. In this case, the backing paper 21b separates the reagent layer 21a from the metal foil 21c. In the moist state heat transfer through the backing paper 21b is, however, readily sufficient to ensure thermal contact within the meaning of the invention. Good thermal contact can also be ensured for other constructions of the test carrier, although the metallic conducting layer and the test field are not in direct contact. They may, for example, be connected by a layer of adhesive or by an interposed liquid transport layer.

Preferably, the surface area of the metallic conducting layer is identical with that of the test field. This provides uniform heating of the whole test field area.

If a test carrier has several test fields that are to be temperature conditioned, as in the case of test fields 21 and 23 of FIG. 2, the appropriate evaluating instrument for this must of course be set up accordingly. In simple cases, in which the test carrier is inserted in the evaluating instrument or transported through this instrument in its longitudinal direction, a single induction heater may suffice. The appropriate test fields are positioned consecutively in the heater's working area.

If the multiple test strips are transported in a direction transverse to their length, in an efficient evaluating instrument, as is shown in FIG. 1, the test fields are evaluated simultaneously in a single measurement position and a separate induction heater must be assigned to each test field that is to be temperature conditioned. If, for example, test field 4 in FIG. 1 also had a metallic conducting layer, a second row of induction heaters would be required, positioned such that the stop positions for test field 4 would be in the heaters' working area.

We claim:

1. An analytical system for measuring the concentration of a component, said system comprising:
   a test carrier having a test field and a metallic conducting layer associated with said test field, said metallic conducting layer lying parallel to the test field and being in thermal contact with the test field, the test field containing a reagent which reacts with said component to produce a measurable change in said test field, said change being accelerated by heat;
   an induction heater having means for producing an alternating magnetic field, said magnetic field having a working area in which a said metallic conducting layer is inductively heated when located therein;
   means for guiding the test carrier so that the metallic conducting layer is in the working area of the alternating magnetic field; and
   an evaluating instrument for measuring a change in the test field after the test field is heated, said change being characteristic of the concentration of the component.

2. The system of claim 1 wherein the metallic conducting layer is ferromagnetic.

3. The system of claim 1 wherein the metallic conducting layer is a metal foil.

4. The system of claim 1 wherein the test carrier is a test strip having a plurality of test fields adjacently disposed thereon, some of said test fields being in thermal contact with a metallic conducting layer.

5. The system of claim 1 wherein the test carrier is a test strip having a plurality of test fields adjacently disposed thereon, two test fields being in contact with respective metallic conducting layers having different thickness.

6. The system of claim 1 wherein the test carrier is a test strip having a plurality of test fields adjacently disposed thereon, two test fields being in contact with respective metallic conducting layers made from different materials.

7. The system of claim 1 further comprising a net, said net securing a test field layer to a base layer with a metallic conducting layer between said layers.

8. The system of claim 1 wherein said guiding means is adapted to cause the test carrier to pause at a plurality of stop points where a test field is in the working area of an alternating magnetic field.

* * * * *